United States Patent [19]

Usui et al.

[11] Patent Number: 5,741,132
[45] Date of Patent: Apr. 21, 1998

[54] MIRROR FOR DENTAL EXAMINATION

[75] Inventors: Masayoshi Usui, Numazu, Japan; Yoshiki Oshida, DeWitt, N.Y.; Seiichi Hata, Hachiouji, Japan

[73] Assignee: Usui Kokusai Sangyo Kaisha Ltd., Japan

[21] Appl. No.: 615,709

[22] Filed: Mar. 13, 1996

[51] Int. Cl.$^6$ ............................................. A61B 1/24
[52] U.S. Cl. ............................................................ 433/30
[58] Field of Search ........................... 433/30, 31; 600/248

[56] References Cited

U.S. PATENT DOCUMENTS

| | | | |
|---|---|---|---|
| 1,387,770 | 8/1921 | Dolbey | 600/248 |
| 1,589,576 | 6/1926 | Thompson | 600/248 |
| 4,993,945 | 2/1991 | Kimmelman et al. | 433/30 |
| 5,139,421 | 8/1992 | Verderber | 433/31 |
| 5,181,848 | 1/1993 | Griffith | 433/30 |

FOREIGN PATENT DOCUMENTS

| | | | |
|---|---|---|---|
| 1027125 | 5/1953 | France | 600/248 |
| 3546379 | 7/1987 | Germany | 433/30 |
| 2266666 | 11/1993 | United Kingdom | 433/30 |
| 4009701 | 5/1994 | WIPO | 600/248 |

*Primary Examiner*—Gary E. O'Connor
*Attorney, Agent, or Firm*—Anthony J. Casella; Gerald E. Hespos; Ludomir A. Budzyn

[57] ABSTRACT

A dental examination mirror is provided. The dental examination mirror includes an examination unit having a planar base wall and a side wall projecting upwardly and outwardly from the base wall. The side wall includes an edge remote from the base wall. A mirror wall is sealingly secured to the edge of the side wall and is substantially parallel to the base wall. The surface of the mirror wall facing away from the base wall are reflective to permit observation of regions in an intraoral cavity. At least portions of the mirror wall enable transmission of light. A light source and a heat source are disposed in the examination unit between the base wall and mirror wall. Light from the light source will be transmitted through at least portions of the mirror wall to illuminate at least portions of the intraoral cavity without shining light toward the eyes of the dentist or patient. The heat source in the examination unit prevents fogging of the mirror.

11 Claims, 6 Drawing Sheets

MIRROR FOR DENTAL EXAMINATION

BACKGROUND OF THE INVENTION

1. Field of the Invention

The present invention relates to a dental mirror which is used for diagnosing and treating the intraoral diseased portion of the patient.

2. Description of the Prior Arts

When the intraoral diseased or affected part of a patient is diagnosed and/or treated, it is required, in many occasions, to examine rear sides of a patient's teeth. Conventionally, a lighting device is provided at the upper front portion of a dental chair and said externally illuminating light is illuminated into the intraoral cavity of the patient. While a dentist manipulates a conventional type of a dental mirror to reflect the externally illuminating light to a portion of the teeth which is needed to be examined, so that the diseased portion can be reflected and displayed on a conventional type of dental mirror.

The aforementioned type of a dental mirror is made of metal, and the reflecting mirror portion and the holding member are formed as a unit structure. Prior to the diagnosing use to each patient, the unified structure of the dental mirror is conventionally sterilized either by an autoclave heating under a high temperature and high pressure or immersing the dental mirror in an antiseptic liquid. However, due to a current situation such as of an intrahospital infection and/or contagion including AIDS, the whole structure of the dental mirror is made of plastic and is used as a disposal type of dental mirror.

Using the aforementioned dental mirror, a diseased portion of the teeth of a patient is required for a dentist to display thereof on a mirror portion by an aid of the externally reflecting light which is illuminating on a mirror surface while the dentist manipulates an incident angle of the externally illuminating light device and reflecting surface of the dental mirror. Accordingly, an appropriate setting of the externally illuminating light device and reflecting surface of the dental mirror is mandatory for performing an accurate dental diagnosis and/or treatment.

As a result, a dentist requires skill to manipulate said dental mirror. There could exist a portion, in particularly the rear sides of the teeth, at which the reflecting light can't reach. In some occasions, a dentist's head might block the illuminating light. By such an occasion, a reflecting angle of the external light is needed to be subjected to a fine-adjustment, in order to maintain a clear examination on the diseased portion. While fine-adjusting the incident angle of the external lighting device, the illuminating light might irradiate a patient's face. Hence, in many cases, not only a patient but also a dentist might be dazzled by the reflecting light or discomfort due to the heat generated by the reflecting light.

On the other hand, since the conventional type of the dental mirror does become foggy due to mainly a humidity and temperature involved in the inhaled air during the respiration activity of a patient when the mirror is inserted into the patient's mouth. Accordingly, once the surface of the dental mirror does become foggy, it becomes difficult to diagnose or treat clearly and properly the diseased portion of the teeth.

Hence, when the dental mirror gets foggy, the dentist takes it away from the mouth, wipes and dries the moisture before the dental mirror is inserted in the mouth again.

As discussed above, the fine-adjustment of the reflecting light to illuminate the reflecting light on the diseased portion of the teeth and cleaning/drying the foggy surface of the dental mirror is inconvenient for the dentist. This situation will prolong the dental chair time required for treating a patient and the dentist can not concentrate on his/her treatment.

SUMMARY OF THE INVENTION

All of the foregoing have resulted in a requirement for the structure and function of the present invention in which it is an objective to provide a mirror for dental examination which prevents a foggy surface when said mirror is used in a humid intraoral environment, and includes a built-in reflecting light device to eliminate an external reflecting light source; so that both patient and dentist will not be dazzled by light and will not feel discomfort due to the heat generated by the external light.

In order to achieve the aforementioned objective of the present invention, an examination unit which is inserted in an intraoral cavity to examine the diseased portion is provided at the distal end portion of the holding member which is held be a clinician while operating thereof. The presently invented mirror for a dental examination is used for diagnosing and treating said diseased portion of the mouth (particularly teeth) by an aid of said examination unit and is further characterized by comprising (1) a light illuminating means to supply an illuminating light to said diseased potion, (2) a mirror portion on which said diseased portion is reflected and displayed by virtue of the reflected light and (3) a heating means to heat said mirror portion.

The present mirror for dental examinations is moreover characterized by that said lighting means and heating means can be structured as a single body or they can be formed separately. It is preferable that the lighting means and heating means are formed as a single body being structured by at least one piece of micro-bulb or a plurality of light emission diode (LED). Alternatively, said lighting means and heating means can be formed separately by an optical fiber and heating member such as a resistance heating member or Peltier element or the like which is placed close to said mirror portion.

In this case, the examination unit and the holding member are fabricated from heat-resistant and corrosion-resistant material and are further characterized by that said examination unit and the holding member can be detachable to each other.

Furthermore, the presently invented mirror for dental examinations is characterized by that a battery which supplies an electric power source to said lighting means and heating means is provided inside the holding member. The battery can be an exchangeable dry battery or non-exchangeable type of chargeable battery.

BRIEF DESCRIPTION OF THE DRAWINGS

The above and many other objectives, features and advantages of the present invention will be more fully understood from the ensuing detailed description of the preferred embodiments of the present invention. That being stated the following description should be read in conjunction with the accompanying drawings wherein;

FIG. 2 are cross sectioned views showing a connecting portion of the examination unit and the holding member of FIG. 1, in which

FIG. 3 are cross sectional views showing a detachable manner with a charging unit according to one embodiment of FIG. 1, in which

FIG. 4 are cross sectional views showing a detachable manner with a charging unit according to another embodiment of FIG. 3, in which

FIG. 5 are views showing an important portion of the second embodiment of the present invention, in which

DETAILED DESCRIPTION OF THE PREFERRED EMBODIMENTS

Figure 1:
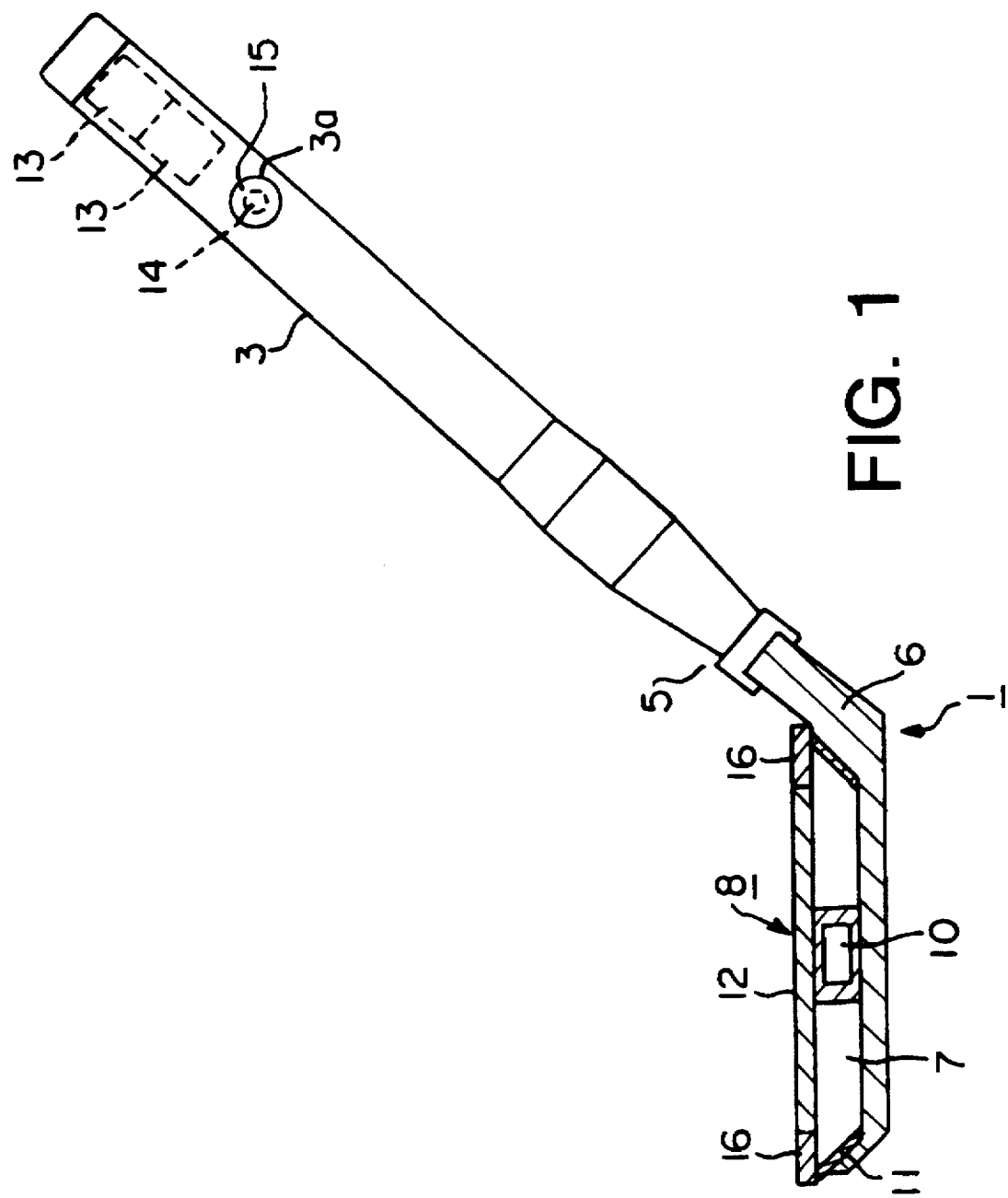
FIG. 1 shows a general view explaining the whole structure of the present invention showing a partially cross-sectioned portion.

Referring back to attached drawings, FIG. 1 shows a general view explaining the whole structure of the present invention showing a partially cross-sectional view. FIG. 2 are cross sectional views showing a connecting portion of the examination unit and the holding member of FIG. 1, in which (a) is a cross sectional view of the holding member side and (b) is a cross sectional view of the examination unit side. FIG. 3 are cross sectional views showing a detachable manner with a charging unit according to one embodiment of FIG. 1, in which (a) is a cross sectional view of the distal portion of the holding member, and (b) is a cross sectional view of the charging unit, and FIG. 4 are cross sectional views showing a detachable manner with a charging unit according to another embodiment of FIG. 3, in which (a) is a cross sectional view of the distal portion of the holding member, and (b) is a cross sectional view of the charging unit.

According to the present invention, the mirror for dental examination is formed as a unit body comprising an examination unit 1 which is inserted in an intraoral cavity of a patient to reflect and display better the diseased portion, and a holding member 3 which is held and operated by a dentist with his/her hand. The examination unit 1 and the holding unit 3 are connected detachably by a connecting component 5.

The examination unit 1 is consisted of a stem portion 6 in which a circular concave portion 7 with a chamfered edge, and an examination mirror portion 8 which is placed in the circular concave portion 7. In the examination mirror portion 8, at least one micro-bulb 10 is fixed in the circular concave portion 7 and a ring-shaped mirror 11 is provided at inner periphery of said circular concave portion 7. An intraoral mirror 12 is fixed above the micro-bulb 10. Furthermore, a transparent ring body 16 is provided at a periphery of said intraoral mirror 12. Moreover, the examination mirror portion 8 is a hermetical structure through the stem portion 6, the intraoral mirror 12 and the transparent ring body 16.

Referring to the electrical power for the micro-bulb 10, although the electric power for the micro-bulb 10 can be supplied by an external battery, it is preferable to provide an electric power source inside the holding member 3; leading to a better operating condition. Hence, according to the present invention, a dry battery or chargeable battery 13 is placed at a portion close to a proximal end portion inside the holding member 3. Said battery 13 is covered with an insulator such as a ceramic or a porous plastic material. An output terminal of the battery 13 is connected to an input terminal of the micro-bulb 10 through the driving button 14. An opening 3a is formed at a periphery position corresponding to the driving button 14 of the holding member 3. A flexible silicone cover 15 seals the opening 3a and is adhered to the holding member 3 in such a manner that the driving button 14 can be pushed in.

Figure 2A:
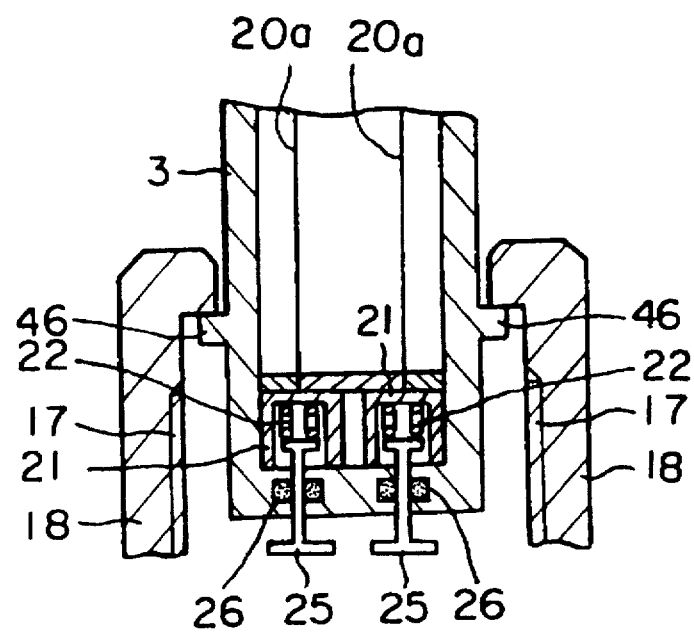
FIG. 2(a) is a cross sectional view of the holding member side and FIG. 2(b) is a cross sectional view of the examination unit side.

Although the examination unit 1 and the holding member 3 can be formed as a unit body structure by connecting these members by the connecting component 5, they can be formed in a detachable manner as seen in FIG. 2. As seen in FIG. 2(a), a ring-shaped projection 46 is formed as a portion of the structure close to the end portion of the holding member 3 on a side of the examination unit 1. A screw 17 is provided at inner surface of said ring-shaped projection 46. A fixing nut 18 is engaged to said screw 17. At a location of the holding member 3 which is close to the examination unit 1, a concave terminal 21 is located in which a lead wire 20a, is fixed. Said lead wire 20a is connected to an output terminal of the battery 13 provided inside the holding member 3. One end portion of a connecting terminal 25 is inserted to the concave terminal 21. Said connecting terminal 25 is provided movably along an axial direction. The connecting terminal 25 is projected from a side of the holding member 3 on the side of the examination unit 1. When the holding member 3 and the examination unit 1 are needed to be detached, the connecting terminal 25 is projected from the end surface of the holding member 3 on the side of the examination unit 1 and is pushed forward toward the projecting direction by a spring 22 which is provided inside the concave terminal 21. An O-ring 26 is placed at a periphery of said connecting terminal 25 to perform a sealing function.

Figure 2B:
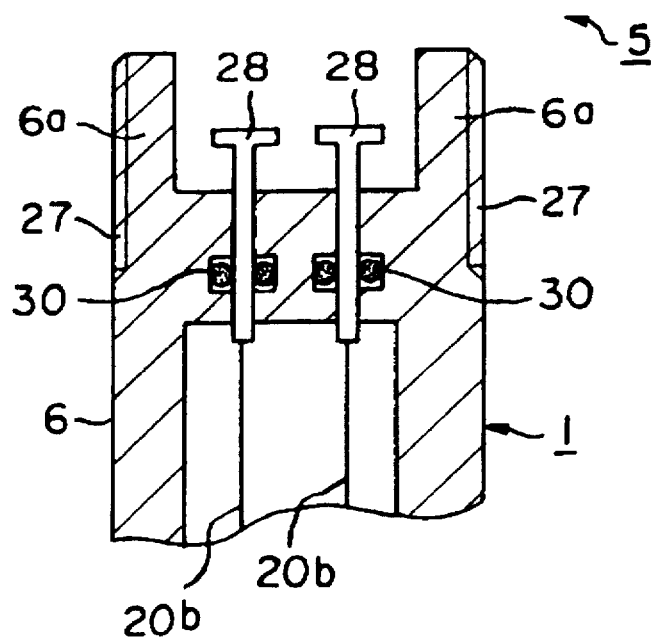

At an end portion of the stem portion 6 of the examination unit 1 at a side of the holding member 3, as seen in FIG. 2(b), a ring-shaped projection member 6a is formed as a portion of the structure. At the outer surface of the ring-shaped projection member 6a, a screw 27 is provided. One end of a connecting terminal 28 being fixed to the stem portion 6 is projected from the bottom surface of the ring-shaped projection member 6a. At a peripheral surface of the connecting terminal 28, an O-ring 30 is provided to function as a sealing effect. The other end of the connecting terminal 28 is connected to one end of a lead wire 20b, while the other end of the lead wire 20b is connected to an input terminal of the micro-bulb 10.

The aforementioned structure of the connecting component 5 can be applied to other portions of the present invention; for example, the stem portion 6 and the examination mirror portion 8 are separately structured and are connected by a detachable connecting component 5. Furthermore, the holding member 3 can be separated into two pieces which can also be connected by the detachable connecting component 5.

Going back to the battery 13, although a dry battery can be chosen as a battery 13 to be placed inside the holding member 3 according to the present invention, a chargeable battery can be used for the battery 13. One embodiment using said chargeable battery, as seen in FIG. 3(b), a charging unit 31 is provided in which an end portion of the holding member 3 can be inserted, in a detachable manner. A battery charger 32 is installed in the charging unit 31. An output terminal 33 of the battery charger 32 is projected toward an opening position 31a which is formed at the upper portion of the charging unit 31.

Figure 3A:
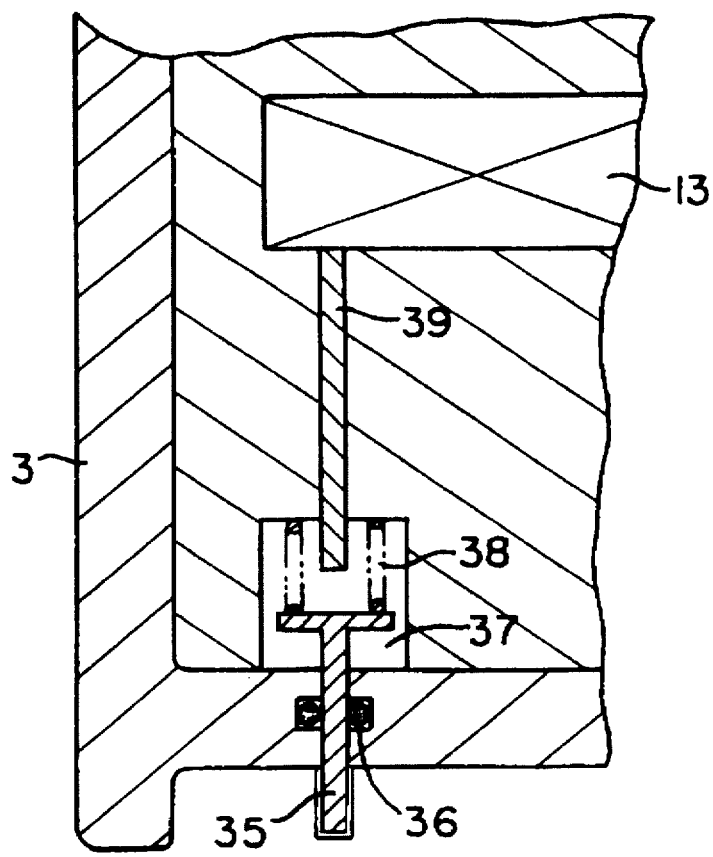
FIG. 3(a) is a cross sectional view of the distal portion of the holding member.
Figure 3B:
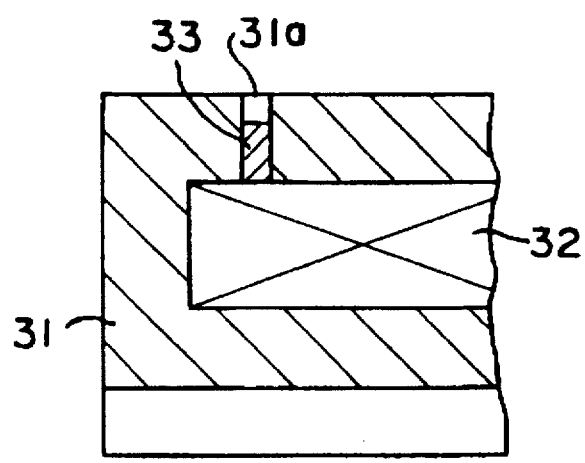
FIG. 3(b) is a cross sectional view of the charging unit.

One end of a charging terminal 35 is projected from an end portion of the holding member 3 which is placed to the charging unit 31, as seen in FIG. 3(a). An O-ring 36 is provided at a periphery of the charging terminal 35. Said charging terminal 35 is movable with respect to the holding member 3 along the shaft direction, and is supported in a sealed condition. The other end of said charging terminal 35 is located inside a connecting chamber 37 which is formed inside the holding member 3. When the holding member 3 is detached from the charging unit 31, the charging terminal 35 is pushed forward toward the projecting direction from the end surface of the holding member 3 under the action of the spring 38 which is provided inside the connecting chamber 37. Furthermore, one end of a connecting terminal 39 being fixed to the holding member 3 is projected inside the connecting chamber 37. The other end of the connecting terminal 39 is connected to the charging terminal of the battery 13.

Figure 4A:
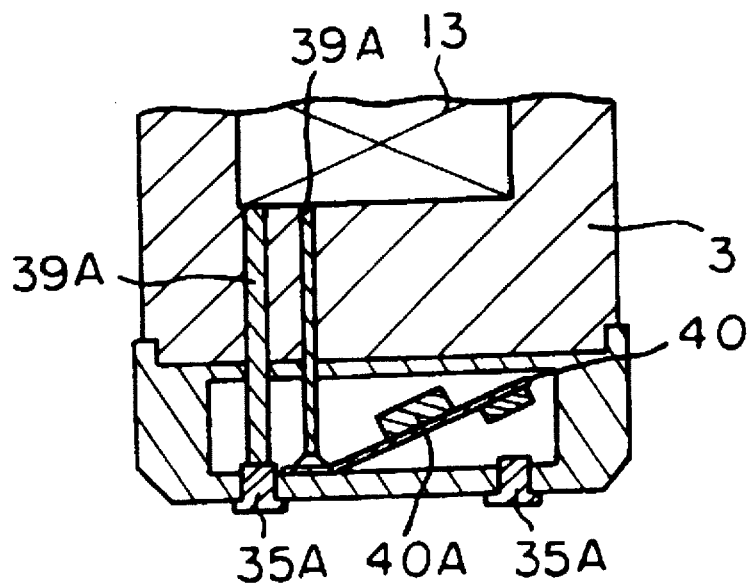
FIG. 4(a) is a cross sectional view of the distal portion of the holding member.
Figure 4B:
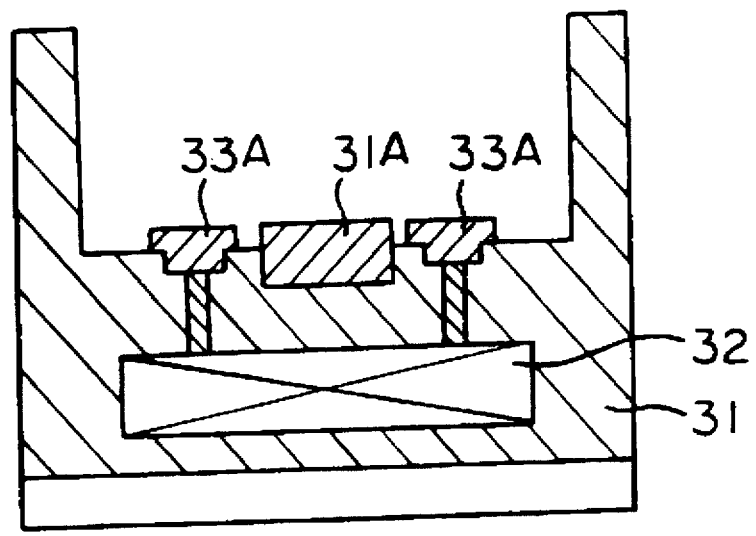
FIG. 4(b) is a cross sectional view of the charging unit.

Another embodiment when a chargeable type of battery is used as a battery can be structured as seen in FIG. 4. Namely, as seen in FIG. 4(b), the charging unit 31 being detachably provided is placed at the end potion of the holding member 3. The battery charger 32 is stored in said charging unit 31. An output terminal 33A of the charger 32 is formed in such a way that the upper surface of the charging unit 31 is exposed. Furthermore, a magnet 31A is provided at nearly the center portion of the upper surface of the charging unit 31.

From the end portion of the holding member 3 which is provided at the charging unit 31, as seen in FIG. 4(a), one end of a pair of charging terminals 35A is projectably provided. One of said charging terminals 35A is connected to one end of the connecting terminal 39A; while the other end of the connecting terminal 39A is connected to one fixed end of a connector 40 which has a spring function inside the holding member 3. Moreover, the other end of the connector 40 is pushed forward toward the opening direction. At the portion near to the center, a magnet 40A is placed opposing to the magnet 31A being placed at the upper portion of the charging unit 31. When the battery having the aforementioned structure is recharged, the holding member 3 is engaged to the upper portion of the charging unit 31 to bring the magnet 31A and magnet 40A in contact by a magnetic attraction force. As a result, other end of the connector 40 becomes in contact to the other end of the charging terminal 35A. At the same time, the charging terminals 35A, 35A are connected to the output terminals 33A, 33A, so that the battery 13 starts to be recharged. Moreover, when the holding member 3 is removed from the charging unit 31, said mirror can now be immediately used. In this embodiment, since the charging terminal 35A does not slide, unlikely as an embodiment shown in FIG. 3, it is not necessary to provide an O-ring. Hence, the reliability and endurance of the mirror structure can be enhanced.

According to the present invention, the stem portion 6 and the holding member 3 of the examination unit 1 are formed by heat-resistant and corrosion-resistant material including metals such as stainless steel, anodized aluminum alloy, titanium or the like, plastics such as PA, PE, PTFE or the like, or inorganic materials such as glass fiber. Although the metallic mirror is employed as the intraoral mirror 12 and the ring-shaped mirror 11 in this embodiment, a conventional type of glass mirror or a plastic mirror being coated with metal may be used as the intraoral mirror 12.

The ring-shaped mirror 11 can be substituted by the circular concave portion 7 in which the inner surface of the outer periphery thereof is mirror-finished. Furthermore, when a glass being coated with a metal is utilized as the intraoral mirror 12, a peripheral portion of the glass component of the intraoral mirror 12 is masked to avoid a coating of the metallic material thereon, so that the intraoral mirror 12 and the transparent ring body 16 can be structured as a single structure.

Having the aforementioned structure, the operational function of the presently invented mirror for dental examination will be described as follows.

A fixing nut 18 which is engaged to the holding member 3 is screw-tightened to the ring-shaped projection member 6a on the shaft portion of the examination unit 1, so that the stem portion 6 is fixed to the holding member 3. By connecting through a screw- tightening, the connecting terminal 28 is pushed in the connecting terminal 25 against the pushing-back force of the spring 22. Accordingly, the battery 13 is connected to the examination unit 1 through the driving button 14. In this embodiment, when said mirror is not used, although the end portion of the holding member 3 is installed in the charging unit 31, the charging terminal 35 is connected into the opening 1a by said installation action, so that the charging terminal 35 is pushed upward by the output terminal 33 against the pushing-back force of the spring 38. As a result, the charging terminal 35 and the connecting terminal 39 are electrically connected. The battery charger 32 charges the battery 13 through the output terminal 33, the charging terminal 35, and the connecting terminal 39. Accordingly, the battery 13 when in use has been recharged enough to perform a proper intraoral examination.

When the intraoral cavity of a patient is examined, the dentist pulls the holding member 3 out of the charging unit 31, inserts the examination unit 1 into the mouth of the patient and pushes the driving button 14, so that the electric power source of the battery 13 is supplied to the micro-bulb 10 to light the micro-bulb 10. By lighting the micro-bulb 10, an illuminating light coming from the micro-bulb 10 is irradiated, the irradiated light is reflected on the ring-shaped mirror 11 and is transmitted through the transparent ring body 16 to illuminate the diseased portion of the patient's mouth.

Moreover, by heat generated by said micro-bulb 10, the back side surface of the intraoral mirror 12 is heated, resulting in that the moisture involved in the inhaled air of the patient is not condensed on the intraoral mirror 12. Accordingly, a foggy surface on the intraoral mirror 12 can be prevented.

Since an optical image of the diseased portion is reflected and displayed on the intraoral mirror 12 without a foggy surface, the dentist is able to examine and treat clearly and accurately the diseased portion of the patient using this intraoral mirror 12 by holding the holding member 3 and moving the examination unit 1 to the diseased portion.

Moreover, when the intraoral examination or treatment is completed, the mirror for the dental examination can be sterilized either by heating in the autoclave at a temperature of 121° C. for 20 min at a pressure of 15 psi or immersing into an antiseptic liquid. According to the present embodiment, since the main body of the mirror for the dental examination is made of heat-resistant and corrosion-resistant material, the battery 13 is covered with an insulator, and the whole structure is a pressure-resisting sealed structure; then components inside the examination mirror 8 or the battery 13 being placed inside the holding member 3 will not be damaged by heat or penetrated antiseptic liquid during the sterilizing process.

In this case, after releasing the connection of the connecting component 5 and removing the examination unit 1 from the holding member 3, only the examination unit 1 can be sterilized by an autoclave-heating or antiseptic immersion treatment.

According to the present invention, it is not required to prepare an external lighting device for illuminating the intraoral cavity and the intraoral mirror 12 does not get fog due to the moisture of the patient's inhaled air, so that a troublesome fine-adjusting of illuminating angle of the light which is caused by blocking the external light by the rear side of the teeth or by a dentist's head can be eliminated and the intraoral mirror 12 is not needed, during the dental treatment, to be removed to dry and clean the foggy surface. As a result, unnecessary additional operations required of the dentist is reduced, so that the dentist can concentrate on his/her diagnosing and treating the patient's teeth with reduced chair-side (treatment) time.

Moreover, the examination unit 1 which is removed from the holding member 3 or a whole structure of said examination unit 1 can be sterilized by autoclave heating or by the antiseptic immersing process, so that simple sterilization can be effectively achieved without causing any damages on the components included inside the examination mirror 8 or the battery installed inside the holding member 3 by the heat during the autoclave sterilization or penetrated antiseptic liquid. Furthermore, when the mirror is not used, the end portion of the holding member 3 is attached to the charging unit 31, so that the battery of the mirror system always recharges. As a result, sufficient electric power source is always supplied to the micro-bulb to avoid a treatment malfunction.

Figure 5A:
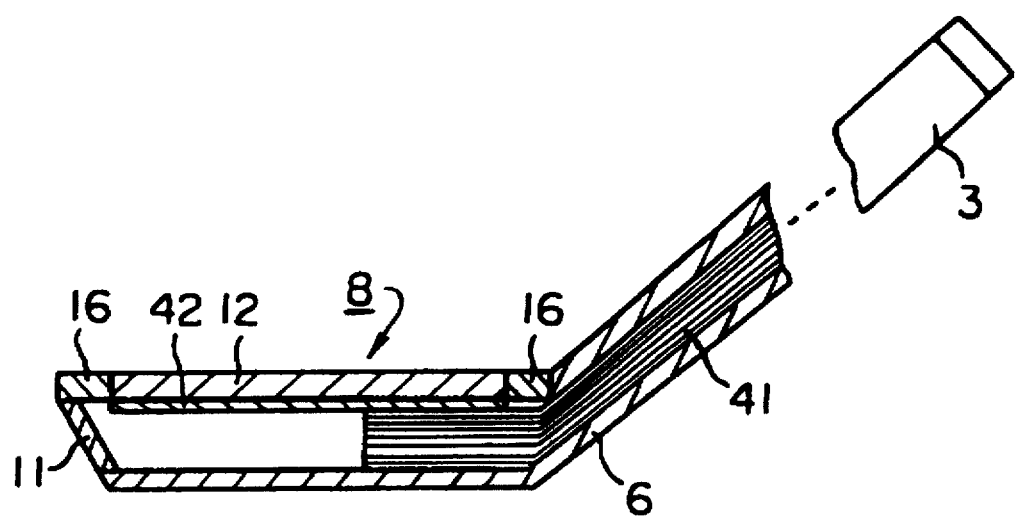
FIG. 5(a) is a cross sectional view and FIG. 5(b) is a plain view showing a partially cross sectional portion.
Figure 5B:
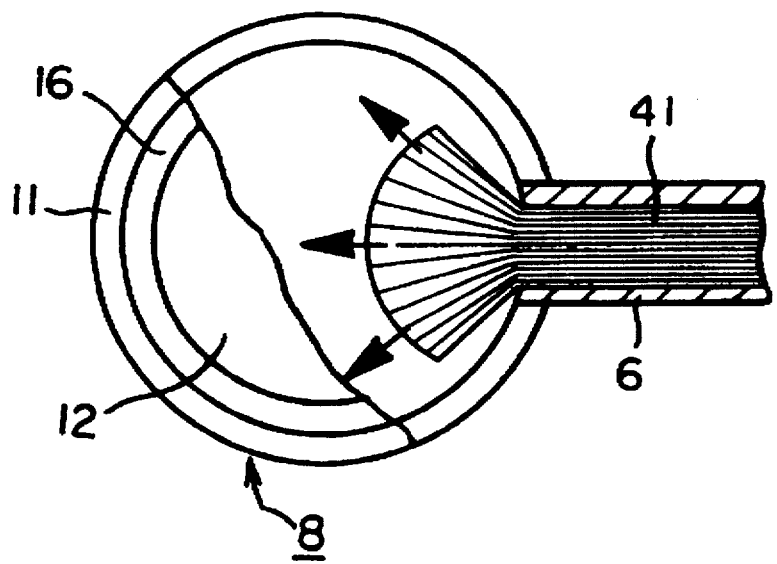

In the next, another embodiment of the present invention will be described referring to FIG. 5. According to the embodiment, in the examination mirror portion 8, a distal end portion of an optical fiber 41 which is longitudinally provided inside the stem portion 6 is placed inside the circular concave portion 7. The distal end portion of said optical fiber 41 is formed with light illuminating means in a fan-shape. The ring-shaped mirror 11 is adhered on the inner periphery of the circular concave portion 7 except the area for inserting the optical fiber. Furthermore, the transparent ring body 16 is provided at the peripheral portion of the intraoral mirror 12 and a resistance-heating member 42 is formed on the rear side of the intraoral mirror 12 in a lamellae manner.

Inside the holding member 3, a light source is connected to the distal end of the optical fiber through the driving button 14. An electric power source is supplied from the battery 13 to the lead wire being longitudinally placed inside the holding member 3 through the driving button 14.

With the aforementioned structure of this embodiment, the light irradiated from the end portion of the optical fiber 41, during the diagnosing and treatment, is transmitted through the transparent ring body 16 and illuminated the diseased portion of the intraoral cavity of the patient. At the same time, the intraoral mirror 12 is heated by the resistance heating member 42.

According to this embodiment, although same effect as the first embodiment as demonstrated in FIGS. 1 through 5 can be realized, additionally by using the optical fiber 41, the illuminating efficiency on the diseased portion can be enhanced.

Figure 6:
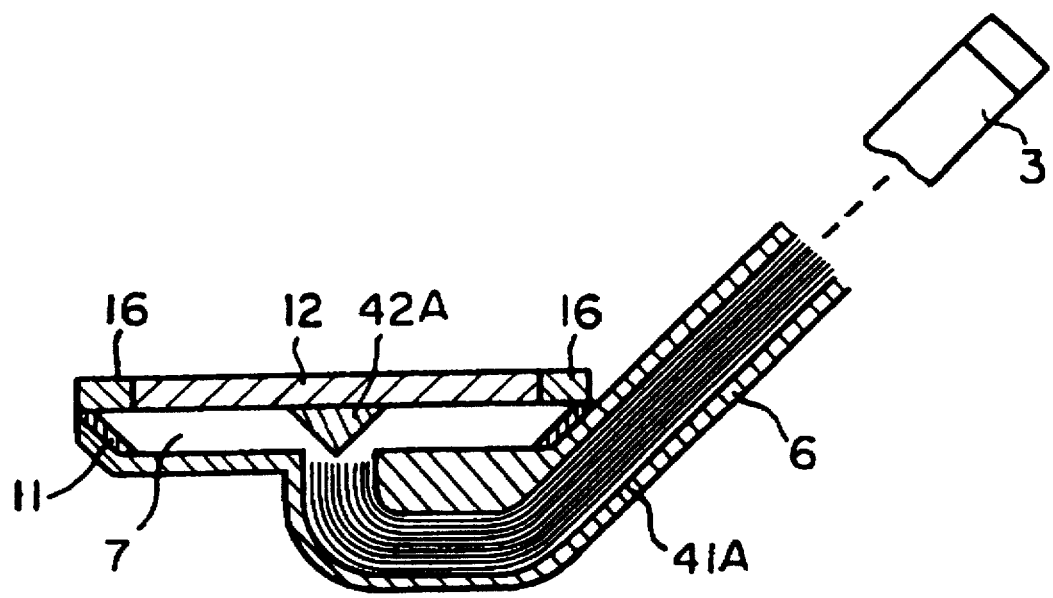
FIG. 6 is a view showing an important portion of the third embodiment of the present invention.

Moreover, the light illuminating means can be formed as seen in FIG. 6. In this embodiment, an optical fiber 41A is elongated to a center position of the circular concave portion 7 and a cone-shaped resistance heating member 42A is provided on the back side of the intraoral mirror 13 facing the end portion of the optical fiber 41A. The top surface of the resistance heating member 42A is mirror-finished.

In this embodiment, the light irradiated from the optical fiber 41A is reflected on the peripheral surface of the cone-shaped resistance heating member 42A. It is further irradiated to the ring-shaped mirror 11 and transmitted through the transparent ring body 16 to illuminate the diseased portion of the patient's mouth. Furthermore, by the resistance heating member 42A, the intraoral mirror 12 can be heated.

According to this embodiment, although the same effect as what has been described for the first embodiment can be achieved, the transmission efficiency of the illuminating light on the diseased portion to be examined can be improved by using the cone-shaped resistance heating member 42A.

Figure 7:
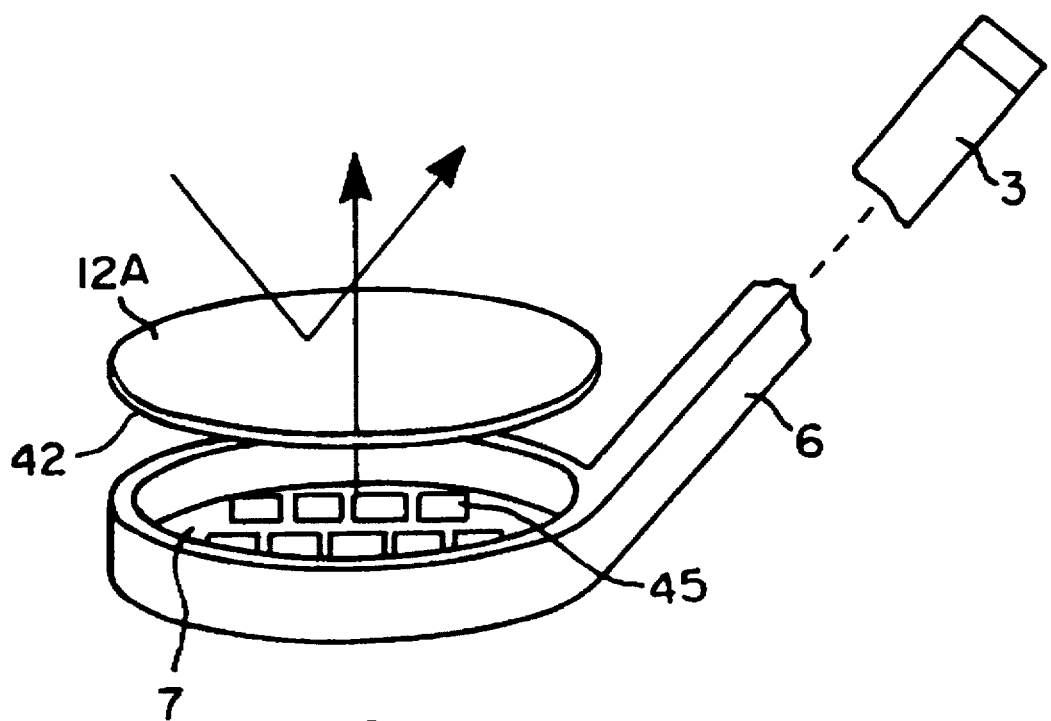
FIG. 7 is an elevated perspective view of an important portion of the fourth embodiment of the present invention.

As another embodiment for the light illuminating means, a structure can be formed as seen in FIG. 7. Referring to FIG. 7, a plurality of light emission diodes (LED) 45 with high brightness is placed on the bottom surface of the circular concave portion 7. To said LED 45, the electric power source is supplied from the battery 13 through the driving button 14 by the lead wire which is longitudinally provided inside the holding member 3. In this embodiment, a half mirror is employed as the intraoral mirror 12A. When the heat generated by said LED 45 is not sufficiently high enough to avoid a condensation of an intraoral moisture of a patient, the resistance-heating member 41 can be placed at the back side surface of the intraoral mirror 12A.

According to this embodiment, the light irradiated from the LED 45 is transmitted through the intraoral mirror 12A which is a half mirror and is illuminated on the diseased portion of the patient's mouth, so that the reflected image of the diseased portion is displayed on the top surface of the intraoral mirror 12A.

Although the same effect obtained by the first embodiment can be achieved from this embodiment, the whole mirror system can be further miniaturized. Although, in the aforementioned embodiment, the resistance heating members 42, 42A are employed as a heating component, the Peltier element can be utilized as a heating member instead of the resistance heating member.

According to the present invention, the examination mirror which is inserted inside the mouth to diagnose and treat the diseased portion of a patient is provided at the distal end portion of the holding member which is held by a dentist during his/her dental clinical performance. The light illuminating means, mirror portion and heating means are provided at the examination unit. The mirror portion which is inserted inside the intraoral cavity is heated by the heating means which is operated by the battery that is installed inside the holding member, so that said mirror portion does not get fog caused by the moisture involved in the inhaled air of the patient during the dental examination and treatment. Furthermore, the diseased portion which is illuminated by the light supplied by the light illuminating means is reflected and displayed on the fog-free mirror portion. Accordingly, additional light supplying devices are not required and the troublesome operation of removing and drying the foggy surface of the mirror can be eliminated. As a result, the diseased portion of a patient's mouth can be accurately and clearly diagnosed and treated without any interruption.

Moreover, since the light illuminating means and heating means are formed by the micro-bulb or the light emission diode, the number of required components can be reduced, so that a whole mirror system can be simplified and miniaturized.

Furthermore, the examination unit and holding member are made of heat-resistant and corrosion-resistant material, so that a sterilization by either autoclave heating or antiseptic immersion process can be easily achieved.

Moreover, since the examination unit and the holding member are structured in such a manner that they are easily detachable, only the examination unit can be effectively sterilized or the examination unit can be disposed if the structural components are not expensive.

If the chargeable battery is utilized, the battery can be automatically recharged while it is not used, by providing the charging unit which is detachably provided at the end portion of the holding member. As a result, a stable power source can always be supplied to the light illuminating means and the heating means from the battery when the mirror system is used.

Furthermore, when the optical fiber is employed as the light illuminating means, and the heating member being placed close to the mirror portion such as the resistance heating member, Peltier element, or the like is utilized as the heating means; the illuminating efficiency on the diseased portion can be enhanced and the whole mirror system can be formed more rigidly.

Moreover, when a half mirror is used for the mirror portion, a light emission diode is employed for the light illuminating means and the resistance heating member being placed close to said half mirror is used as the heating means; a whole mirror system can be structured with a simpler and smaller structure.

While the invention has been explained with reference to the structure and function disclosed herein, it is not confined to the details as set forth, and this application is intended to cover modifications and changes as may come within the scope of the following claims.

What is claimed is:

1. A mirror for dental examination comprising: an elongate holding member formed from a corrosion resistant, heat resistant material and having a proximal end for griping by a dental examiner and an opposed distal end; and an examination unit comprising a housing formed from a corrosion resistant, heat resistant material and comprising a planar base wall, a side wall projecting upwardly and outwardly from said planar base wall, said side wall having a reflective inwardly facing surface and a substantially circular edge on portions remote from said base wall, a stem projecting from said side wall and secured to said distal end of said holding member, a substantially planar mirror wall sealingly secured to said circular edge of said side wall and disposed in spaced parallel relationship to said planar base wall, said mirror wall including a mirrored surface facing away from said base wall and a light transmitting portion disposed at least on portions of said mirror wall adjacent said circular edge, and illuminating disposed between said mirror wall and said planar base wall for directing light toward the reflective surface of said side wall and heating means, separate from said illuminating means, for heating said mirror, whereby light from said illuminating means reflects from said reflective surface of said side wall and is transmitted through said light transmitting portion of said mirror wall for illuminating selected portions of an intraoral cavity, and whereby said heating means heats said mirror for preventing fogging.

2. The mirror of claim 1, wherein the illuminating means comprise a plurality of optical fibers.

3. The mirror of claim 2, wherein the optical fibers comprise end portions extending substantially parallel to the planar base wall.

4. The mirror of claim 3, wherein the optical fibers extend through said holding member and said stem, portions of said optical fibers spaced from said stem diverging from one another into a generally fan-shape.

5. The mirror of claim 2, further comprising a resistance heating element affixed to surface regions of said mirror wall facing said planar base wall.

6. The mirror of claim 2, wherein said ends of said optical fibers comprise end portions extending substantially orthogonally through said base wall.

7. The mirror of claim 6, wherein the mirror wall further comprises a cone-shaped resistance heating member on a surface of said mirror wall facing said optical fibers, said cone-shaped resistance heating member reflecting light from said optical fibers toward said reflective surface of said side wall.

8. The mirror of claim 1, wherein the heating means comprises a resistance heating member.

9. The mirror of claim 1, wherein the mirror wall is a half mirror, said mirrored surface extending across substantially all of said mirror wall facing away from said base wall, such that substantially all of the surface of said mirror wall facing away from said base wall reflects images of said intraoral cavity, said light transmitting portion extending across substantially all of said surface of said mirror wall facing said base wall, such that substantially all of the surface of said mirror wall facing said base wall transmits light from said illuminating means.

10. A mirror for dental examination of an intraoral cavity, said mirror comprising an elongate holding member having a proximal end for manipulation by a dental examiner and a distal end, an examination unit secured to said distal end of said holding member, said examination unit comprising a planar circular base wall, a side wall projecting upwardly and outwardly from said base wall, said side wall including a concave inner surface and a circular edge spaced from said planar base wall, a stem projecting from said side wall and comprising means for the secure connection of the examination unit to the distal end of the holding member, a generally ring-shaped mirror affixed to said concave inner surface of said side wall, illuminating means disposed substantially adjacent portions of said base wall surrounded by said side wall for generating light, said illuminating means comprising at least one light emitting diode in said examination unit, a planar half mirror secured to said edge of said side wall and substantially parallel to said planar base wall, said half mirror having a surface facing said base wall for transmitting light from said illuminating means and having a reflective surface facing away from said base wall for reflecting light externally of said examination unit, and heating means in proximity to said half mirror for preventing fogging of said half mirror, said heating means comprising a resistance heater disposed substantially adjacent said inner surface of said half mirror.

11. The mirror of claim 10, further comprising a battery and a switch disposed in said holding means and operatively connected to said illuminating and heating means.

* * * * *